United States Patent [19]

McCormick et al.

[11] Patent Number: 4,743,537
[45] Date of Patent: May 10, 1988

[54] BIOLOGICAL INDICATOR FOR STERILIZATION PROCESSES

[75] Inventors: Patrick J. McCormick; John R. Scoville, Jr., both of Henrietta, N.Y.

[73] Assignee: Castle Company, Rochester, N.Y.

[21] Appl. No.: 942,506

[22] Filed: Dec. 24, 1986

Related U.S. Application Data

[63] Continuation-in-part of Ser. No. 820,354, Jan. 21, 1986, Pat. No. 4,717,661.

[51] Int. Cl.$^4$ ............................................. C12M 1/24
[52] U.S. Cl. ................................. 435/296; 435/31; 435/289; 435/810
[58] Field of Search .............. 435/31, 289, 287, 296, 435/299, 300, 805, 810, 832, 839, 842

[56] References Cited

U.S. PATENT DOCUMENTS

| | | | |
|---|---|---|---|
| 3,346,464 | 10/1967 | Ernst | 195/54 |
| 3,661,717 | 5/1972 | Nelson | 195/103.5 R |
| 3,752,743 | 8/1973 | Henshilwood | 195/127 |
| 4,291,122 | 9/1981 | Orelski | 435/31 |
| 4,304,869 | 12/1981 | Dyke | 435/296 |
| 4,345,028 | 8/1982 | Nelson et al. | 435/30 |
| 4,461,837 | 7/1984 | Karle et al. | 435/296 |
| 4,528,268 | 7/1986 | Anderson et al. | 435/31 |
| 4,579,823 | 4/1986 | Ryder | 435/296 |
| 4,596,773 | 6/1986 | Wheeler | 435/31 |

Primary Examiner—Margaret A. Focarino
Attorney, Agent, or Firm—Marjama & Pincelli

[57] ABSTRACT

A sterility indicator which comprises means defining an elongated outer compartment having liquid impermeable and substantially non-gas absorptive walls, said compartment having a closed end and a first opening at a distal end thereof and a second opening which is gas transmissive and bacteria-impermeable disposed at least partially around the perimeter of said outer compartment and located near said first opening, with a predetermined number of viable microorganisms suitable for monitoring steam sterilization being confined within said outer compartment adjacent said second opening, and a predetermined number of viable microorganisms suitable for monitoring gas sterilization being confined within said outer compartment away from said second opening and opposite said distal end; a closure member normally closing said first opening and movable to a second position to also close said second opening; and an inner compartment containing a nutrient medium disposed within said outer compartment with said nutrient medium being out of direct contact with said microorganisms, said inner compartment being adapted to open in response to external pressure thereby permitting said nutrient medium to contact said microorganisms.

5 Claims, 3 Drawing Sheets

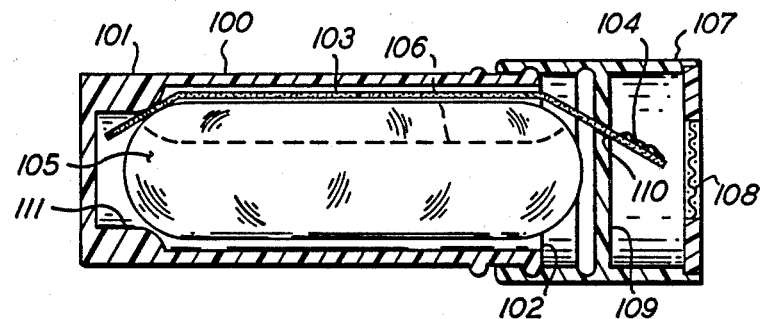
FIG. 5
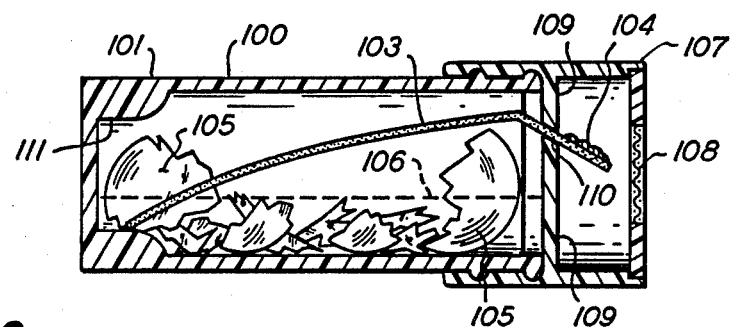
FIG. 6
FIG. 7
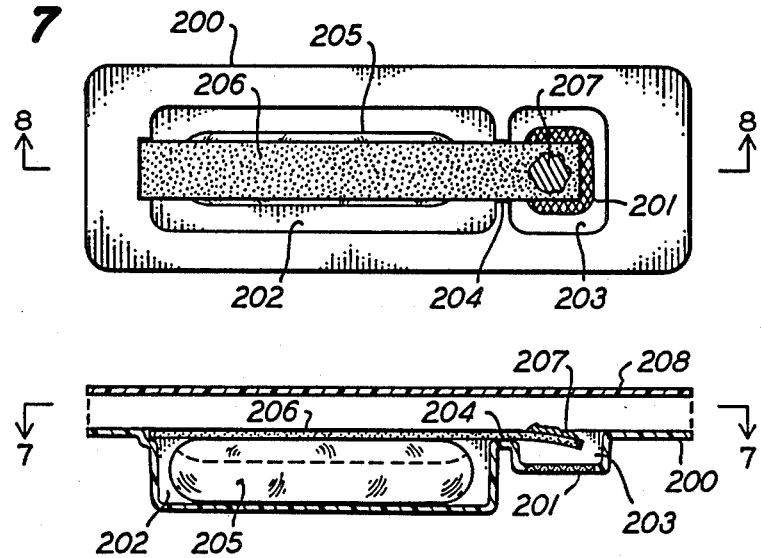
FIG. 8

BIOLOGICAL INDICATOR FOR STERILIZATION PROCESSES

This is a continuation-in-part of Application Ser. No. 820,354, filed Jan. 21, 1986, and now U.S. Pat. No. 4,717,661.

BACKGROUND OF THE INVENTION

The invention relates to a biological indicator suitable for use in monitoring the efficacy of a sterilization process.

In the sterilization of medical instruments and related hardware it is essential to determine whether a particular batch of articles which has been subjected to a sterilizing environment, such as steam or gas, has in fact been effectively sterilized. A common art recognized technique for carrying out this objective involves subjecting a known number of test microorganisms of resistance to the sterilant employed to the same sterilizing conditions to which the articles in the sterilizer are subjected. At the end of the sterilization cycle, the microorganisms are removed from the sterilizer and exposed to a nutrient culture medium. The microorganisms are incubated for a specified time period and then checked for growth of microorganisms. If no growth of the microorganism occurs, then it is assumed that articles in the sterilizer have been properly sterilized for their intended use. However, if growth has occurred, the articles are determined not to be sterile and should be subjected to a second sterilization cycle.

One commercial embodiment of biological indicators is the spore strip. This device comprises a calibrated spore population inoculated on a paper chromatography grade carrier, and enclosed in a microorganism impermeable glassine envelope. Alternative carrier or envelope materials could be employed. Spore strips require a person to conduct an aseptic transfer of the carrier to presterilized nutrient medium before incubation. Performance standards developed for biological indicators by recognized authorities such as the Association for the Advancement of Medical Instrumentation, are based on glassine spore strip performance characteristics.

A second commercial embodiment of biological indicators is the unitary or self-contained biological indicator. These devices comprise a microorganism impermeable package containing a nutrient medium, and a calibrated spore population inoculated on a suitable carrier material. The aseptic transfer for unitary or self-contained biological indicators is conducted within the microorganism impermeable package as opposed to the case of spore strips where the carrier is removed from the outer packaging materials.

At least two aspects in the construction of biological indicators can influence the kill rate of the calibrated spore population. The first being thermal mass, and the second being the permeation rate of sterilant to the spores. In unitary or self-contained biological indicators, the additional thermal mass provided by the nutrient medium and other packaging materials causes performance characteristics which are different from glassine spore strips. This poses a problem for self-contained biological indicators since the authoritative standards for biological indicator performance are based on glassine spore strips.

One of the first unitary or self-contained biological indicators was described in U.S. Pat. No. 3,346,464. This patent teaches a sterilization indicator in the form of a semi-permeable envelope which is capable of transmitting water and a gaseous sterilizing media without allowing the passage of microorganisms. The envelope contains both test microorganisms and a dehydrated nutrient media. After exposure to a sterilization cycle, the envelope is immersed in warm water. The water permeates the envelope and rehydrates the nutrient media allowing for contact with the test microorganisms, allowing for growth of any remaining viable microorganisms. This structure, however, suffered from a number of design defects and did not achieve wide success. For example, the performance of this device was dependent upon the characteristics of the water in the warm water incubation, which could vary in purity from test to test. In addition, the permeable envelope was vulnerable to entrapping undesirable quantities of sterilizing gas.

More recent improvements to unitary or self-contained biological indicators are illustrated by U.S. Pat. Nos. 3,661,717 and 4,291,122. Both of these patents, however, teach devices which suffer performance anomalies over a range of sterilization temperatures from 270° F.–285° F. (Reich, R. R. and Fitzpatrick, B. G., Journal of Hospital Supply, Processing and Distribution, May-June 1985, vol. 3, No. 3, pp. 60–63). These performance anomalies are due to thermal lag caused by their design and construction (Joslyn L. Sterilization by Heat, in Disinfection, Sterilization and Preservation. Block.S. Eds. Lea & Febiger. Phila., Pa. 1983 pp. 33–34). Common to both the U.S. Pat. Nos. 3,661,717 and 4,291,122 patents is that they both provide for an outer compartment or vial containing a pressure openable inner compartment (i.e., the media ampule) with the microorganisms or spores on their respective carriers located between and adjacent to the two compartments. It is this disposition of the spores between the two compartments and their close juxtaposition with the ampule of media which retards the penetration of the sterilant, augmenting the effect of thermal lag thereby contributing to the performance anomalies of these indicators. Investigations have shown and inferences from the literature (Perkins et al., Applied and Environmental Microbiology Aug., 1981, Vol. 42, No. 2, pp. 383–384) indicate that the sterilization times required at temperatures at or above 270° F. for conventional self-contained biological indicator designs are excessive in comparison to conventional biological indicator designs consisting of spores inoculated onto a paper chromatography grade carrier (or other suitable carrier) and enclosed in a glassine or other suitable material envelope. This can result in "false positive" readings and lead to the reprocessing of an otherwise sterile load and unnecessary equipment downtime. "False negative" readings can also occur at lower sterilization temperatures (240 degrees F. to 245 degrees F.) leading to release as sterile of an underprocessed load whose contents may in fact not be sterile (Reich and Fitzpatrick, ibid).

Specifically, it is an objective of the present invention to provide a self-contained biological indicator whose design circumvents the drawbacks noted above and whose performance characteristics more readily approximate those of a conventional biological indicator than the currently available commercial self-contained biological indicators. This performance over a range of sterilization temperatures may be defined as "The Z-value, measured in degrees of temperature, is the temperature coefficient of microbial destruction and is the time for the D-value or sterilization time of microorganisms to change by a factor of ten." ("Pflung, I. J. and Smith, G. M., The Use of Biological Indicators for Monitoring Wet Heat Sterilization Processes in Sterilization of Medical Products, Eds. E. R. Gaughran and K. Kerluck, Johnson & Johnson 1977).

It is the intent of the device of the present invention to perform with a z-value more closely approximately that of conventional biological indicators and published z-values for *B. stearothermophilis.* of 18°–20° F. (*The Destruction of Bacterial Spores,* A. D. Russell, Academic Press, 1982).

Commercially available self-contained biological indicators tested in our laboratories have been found to exhibit Z-values as high as 80 degrees F. as opposed to 18–20 degrees F. for conventional paper strip biological indicators enclosed in glassine envelopes. Proto-types prepared in the manner described by this invention have exhibited Z-values ranging from 20–30 degrees F. and to closely parallel the performance of conventional biological indicators as opposed to the commercially available self-contained biological indicators described above.

SUMMARY OF THE INVENTION

The present invention is directed to overcoming the above described problems associated with sterility indicators of the "self-contained" biological type by providing a device that assures direct impingement of the sterilant onto the microorganisms. In this manner, the sterilant exposure conditions experienced by the test organisms should reflect the exposure conditions to which the articles in the sterilizer are subjected to a greater degree than existing self-contained biological indicators.

The device of the invention also provides that the microorganisms are not directly contiguous with the ampule containing the aqueous nutrient medium.

In a preferred embodiment, the invention further eliminates the loss of water vapor by evaporation of the culture medium by providing a sealing means for the test device after the device has been subjected to a sterilization cycle, thereby allowing incubation of the device at elevated temperature (i.e., 55 degrees C.) without significant loss of culture medium.

The present invention provides a self-contained biological indicator device suitable for use in a sterilization process and comprises the following features:

Specifically, the device comprises an outer compartment having at least one open end. The device contains at least one permeable opening or window which permits the transmission of sterilant gas or steam while preventing the transmission of microorganisms into or out of said compartment. The compartment further contains a frangible ampule containing a sterile liquid culture medium. The indicating microorganisms are disposed on one end of an absorbant wick or other suitable carrier material. The end of the wick containing the microorganisms is disposed away from the media containing ampule and adjacent the sterilant permeable window.

A substantially non-gas absorptive and liquid-impermeable closure member or cap is provided to seal the open end of said compartment. The device also contains internally a detector or a pH indicator material which undergoes a visible color change in response to growth of the microorganisms.

During sterilization, the end of the wick containing the disposed microorganisms located opposite the sterilant permeable window is exposed to direct impingement of the sterilant.

Upon completion of the sterilization process, the device is removed from the sterilizer and the cap is moved to the second position or closed position, sealing the permeable window and thus preventing the evaporation of media. The ampule is then broken by applying pressure to the outer compartment, thereby releasing the culture medium into the compartment. The culture medium is absorbed by the wick and transported to the end of the wick containing the microorganisms, thereby establishing a continuum between the microorganisms and the medium. The device is then incubated by appropriate techniques well known to the art, and then examined to determine via color change or turbidity of the culture media whether or not growth of the microorganisms has taken place.

Other features and advantages of the present invention will become apparent from the following description taken in conjunction with the accompanying drawings.

BRIEF DESCRIPTION OF THE DRAWINGS

FIG. 5 is a longitudinal sectional view of a second embodiment of a device of the present invention.

FIG. 6 is a longitudinal sectional view of the device of FIG. 5 in the activated position after sterilization.

FIGS. 7 and 8 represent plan and side views of a further embodiment of the device of the present invention.

DETAILED DESCRIPTION OF THE INVENTION

Figure 1:
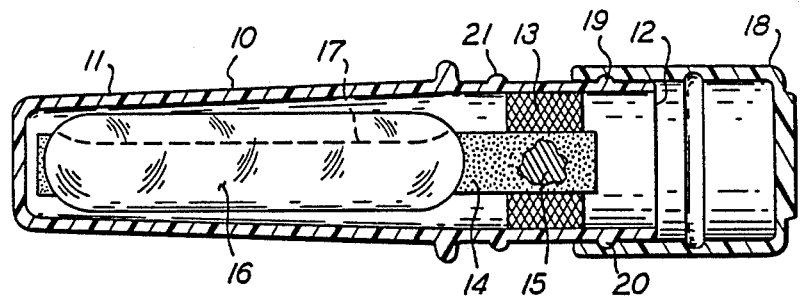
FIG. 1 is a longitudinal sectional view of one embodiment of the device of the present invention.
Figure 2:
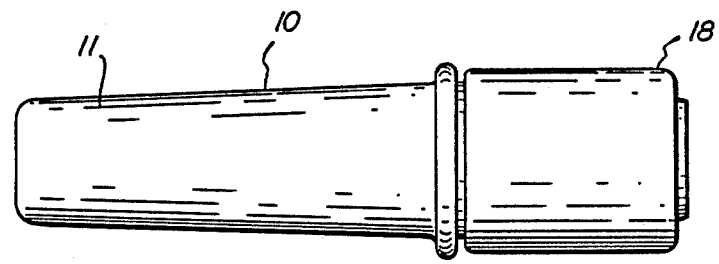
FIG. 2 is a side elevation view of the device of FIG. 1 with the closure member in the closed position.
Figure 3:
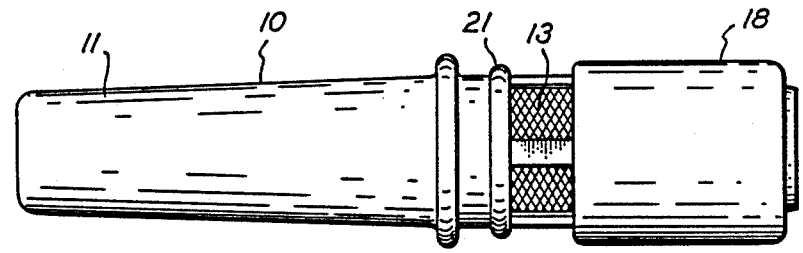
FIG. 3 is a side elevation view of the device of FIG. 1 with the closure member in the open position.

Referring to FIG. 1, a sterility indicator device is shown having an outer compartment comprising a flexible transparent or translucent, cylindrical tube 10, having substantially non-gas absorptive and liquid-impermeable walls 11 and an open end 12. Compartment 10, further contains a gas transmissive, bacteria impermeable window in the form of a submicron screen or other suitable material 13 at one end thereof. Compartment 10 further contains a suitable carrier such as an absorbant wick 14 bearing a pre-determined number of viable microorganisms, or bacterial spores. The microorganisms, illustrated by shaded area 15, are confined to one end of wick 14. Compartment 10 also contains, in coacting relationship therewith, a normally sealed, pressure-openable inner compartment 16, such as a frangible glass ampule, containing an aqueous nutrient medium illustrated by dotted line 17 which is capable, with incubation, of promoting growth of the microorganisms when contacted therewith. The end of the wick containing the microorganisms is located away from the media containing ampule and adjacent to screen 13. A substantially non-gas absorptive and liquid-impermeable closure member or cap 18 is provided to seal the open end 12 of compartment 10. In FIGS. 1 and 3, the cap is shown in the open position and is engaged to be moved to a second or closed position illustrated by FIG. 2. In the closed position the permeable window is sealed thus preventing the evaporation of media. As shown, the cap 18 is engaged in a pressure snap fit relationship with compartment 10 by recess 19 engaging ridge 20. To close the cap, longitudinal pressure forces the flexible sidewalls of the cap to expand or deflect slightly and allow the cap to move to a second or closed position in which recess 19 now engages ridge 21.

The aqueous nutrient 17 also contains a detector or pH indicator material (not shown) which undergoes a visible color change in conjunction with a turbidity of the medium in response to growth of the microorganisms. During sterilization the microorganisms located in a position opposite the screen are exposed to direct impingement of the sterilant. Upon completion of the sterilization process, the device is removed and the cap moved to the closed position and the ampule is broken by applying pressure through the flexible side of the device releasing the culture medium into the compartment. The culture medium is absorbed by the carrier material and transported to the end of the carrier containing the microorganisms.

The device is then placed into an incubator or other constant temperature environment to permit the growth of any surviving microorganisms. After a suitable growth period, the device is examined to determine from the color of the indicator or turbidity of the medium used whether or not growth had taken place.

Any microorganisms not killed during the sterilization process begin to germinate and grow during incubation, causing turbidity and/or the indicator material to change color. This color change is observed through the transparent/translucent walls of compartment 10, and indicates to an observer that the sterilization cycle had not killed all of the microorganisms on the wick and hence was insufficient to assure sterilization of the other items in the sterilizer. An absence of turbidity or a color change indicates that the sterilization cycle had killed all of the microorganisms on the wick and was sufficient to assure sterilization of the items in the sterilizer.

Figure 4:
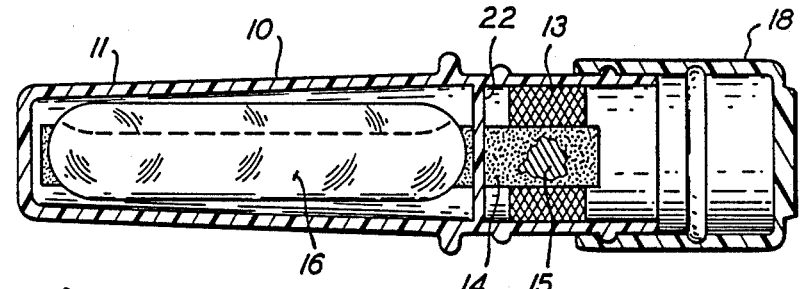
FIG. 4 is a longitudinal sectional view of the device of FIG. 1 slightly modified.

FIG. 4 illustrates a further embodiment of the present invention which is a modification of the device of FIG. 1. In this embodiment, a barrier wall 22 is disposed at the end of compartment 10 and physically separates the end of the wick containing the microorganisms from the opposite end of the wick which is adjacent the media containing ampule. The wick connects both chambers through an opening or channel (not shown) in wall 22. This structure provides the advantage of further isolating the microorganisms from the media containing ampule in a third compartment independent of the first (10) and second (16) compartments.

A second embodiment of the present invention is illustrated in FIGS. 5 and 6.

Referring to FIG. 5, a sterility indicator device is shown having an outer compartment comprising a rigid transparent or translucent, cylindrical tube 100, having substantially non-gas absorptive and liquid-impermeable walls 101 and an open end 102. Compartment 100 further contains a suitable carrier such as an absorbant wick 103 bearing a pre-determined number of viable microorganisms. The microorganisms, illustrated by enlarged area 104, are confined to one end of wick 103. Compartment 100 also contains, in coacting relationship therewith, a normally sealed, pressure-openable inner compartment 105 in the form of a frangible glass ampule, containing an aqueous nutrient medium illustrated by dotted line 106 and which is capable, with incubation, of promoting growth of the microorganisms when contacted therewith. A substantially non-gas absorptive and liquid-impermeable closure member or cap 107 is provided to seal the open end 102 of compartment 100. Cap 107 contains a gas transmissive, bacteria impermeable window in the form of a submicron screen 108 at one end thereof. In FIG. 5, the cap is shown in a first position and is frictionally engaged to be moved to a second or closed position illustrated by FIG. 6. The end of the wick containing the microorganisms is located away from the media containing ampule and adjacent screen 108 with the end of the wick being segregated from compartment 100 by wall 109. The wick is sealed in and passes through hole 110 contained in wall 109.

During sterilization, the microorganisms which are confined in a position opposite the screen are exposed by direct impingement of the sterilant. Upon completion of the sterilization process, the device is removed from the sterilizer and the ampule is broken by applying pressure along the vertical axis of the device. This pressure allows wall 109 to force ampule 105 into the restricted portion 111 at the bottom of compartment 100 and fracture the glass ampule as illustrated in FIG. 6.

In an alternative embodiment of the present invention as illustrated by FIGS. 7 and 8, the device may be in the form of an outer plastic shell 200 which may be injection molded of polypropylene or some other suitable plastic. The shell contains a submicron screen 201 and is divided into two separate compartments 202 and 203 as illustrated by FIGS. 7 and 8. The shell is further provided with a shallow channel 204 which connects the two compartments.

A media ampule 205 is contained in compartment 202 and a wick 206 is disposed within compartments 202 and 203 with the microorganism 207 being confined to one end of the wick adjacent screen 201.

As illustrated by FIG. 8, a top film of suitable plastic 208 is bonded adhesively or by a heat seal to shell 200. This embodiment functions in the same manner as the other embodiments with the advantage of locating the microorganisms adjacent the screen.

Figure 9:
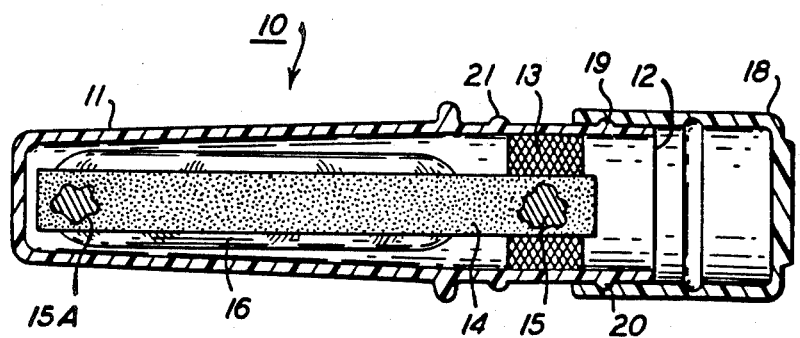
FIG. 9 is a longitudinal sectional view of a further embodiment of the present invention.

In a further embodiment of the present invention it has been found that certain advantages are obtained by separating microorganisms for steam and gas sterilization respectively. In this embodiment, illustrated by FIG. 9, microorganisms 15 suitable for monitoring steam sterilization are positioned at the end of the wick adjacent the gas transmissive and bacteria - impermeable opening to allow for the advantages of direct impingement, while the microorganisms 15A, separated by an area devoid of monitoring microorganisms from microorganisms 15, and suitable for monitoring ethylene oxide or gas sterilization are confined to and positioned at the opposite end of the wick. It should also be understood that this embodiment is also applicable to the configuration illustrated in FIGS. 7 and 8.

The gas or ethylene oxide sterilization process is more complex than that for steam. Lethality of the gas or ethylene oxide sterilization process depends on the integration of gas concentration, relative humidity, temperature and exposure time. Since the ethylene oxide sterilization process temperatures are low (130° F.) relative to steam sterilization (250°-285° F.) and the exposure times much longer (minimum 2 hours) than with steam sterilization, the effect of thermal mass represented by the ampule is negligible with respect to delivered lethality. In conventional glassine spore strips, the glassine functions as a diffusion barrier to ethylene oxide and relative humidity passage where as the gas transmissive, bacteria impermeable window lacks these same diffusion characteristics. Direct impingement of sterilant and relative humidity on the gas or ethylene oxide monitoring microorganisms, has been found to cause accelerated microbial kill versus the glassine spore strip. Since standards for biological indicator performance are based on glassine spore strips, the location of steam, and ethylene oxide monitoring microorganisms of this embodiment, is preferred in order to more closely approximate the performance of conventional biological indicators.

Microorganisms suitable for use with the device of the present invention are the spore forms of *Bacillus* and *Clostridium* genera such as: *B. subtilis var. niger, B. subtilis var. globigii, B. stearothermophilus, B. coagulans,* and *Clostridium sporogenes.* The microorganisms of choice for one preferred embodiment are *Bacillus stearothermophilus* (American Type Culture Collection #7953 or #12980) for steam processes and *Bacillus subtilis var. niger* (American Type Culture Collection #9372) for ethylene oxide or other gaseous sterilization processes. Both of these microorganisms may preferably be contained in the same biological indicator thus having a commercial embodiment for a single process indicator that can monitor either steam or gas sterilization. The microorganisms may be suspended in a dispersion or medium when they are applied to the carrier in the fabrication process. J. E. Doyle in his 1971 article in the Bulletin of the Parenteral Drug Association, volume 25, pages 98 to 104, describes one such medium. Other satisfactory mediums include a wide variety of aqueous, and organic mixtures.

Materials that are acceptable for the cylindrical tube, cap, and other plastic structural components for the device of the present invention must be substantially sterilant impermeable and be able to withstand gaseous and/or steam sterilization processes as currently applied in the medical field. Materials should be biologically inert as to have minimal influence on the recovery of sterilization stressed microorganisms and deformable, in the preferred embodiment, so that the fragile inner compartment may be ruptured with finger pressure. The cylindrical tube must be either transparent or translucent so that effects of any microorganism growth may be viewed from the outside. Preferred materials include polypropylene or polypropylene copolymers, such as Himont Inc. Pro-Fax 7523 or Pro-Fax 6323 resins. Nylons, thermoplastic polyethylene terephthalate, and the fluoroplastics i.e. polytetrafluoroethylene, are examples of alternative materials that could also be used.

The submicron screen is an extension of the cylindrical tube and as such it must have similar physical properties. An exception to this requirement is that the submicron screen must readily pass sterilant vapors while still being a barrier to biological contamination of the cylindrical tube's inner space from external sources. Pore sizes in the submicron screen may range up to 0.45$\mu$ meters. Numerous materials are candidates for the submicron screen are commercially available including: polytetrafluoroethane, acrylic copolymer with a nylon support medium, polypropylene, and polysulfone. Gore-Tex Versapore 450, manufactured by Gelman Sciences Inc., is a suitable material. Alternatively, materials describing a tortuous pathway (as opposed to a defined porosity) to inhibit microbial penetration while allowing passage of sterilant vapors may also be employed in lieu of a submicron screen. Such materials are well known in the medical device industry.

The preferred means to achieve a fragile inner compartment is through the use of an onion skin glass ampule. This is a round cylindrical glass container with round ends. The glass wall thickness is typically 0.2 millimeters. Glass compositions which are suitable for use comprise either type 1 - borosillicate, or type 111 - soda lime glass. Because the ampule is flame sealed after being filled with culture medium in the manufacturing process, the ampule is not totally filled with culture medium. The remaining volume is filled with a gas such as air, nitrogen, helium, argon, or carbon dioxide, and a water vapor component. The absolute pressure of the gas contained in the head space is lower than atmospheric pressure because of the sealing process.

The carrier or wick functions as the substrate upon which the microorganisms are inoculated and also as the means by which the microorganisms are positioned so that substantially direct impingement of sterilant may occur. It is also the transport vehicle by which microorganisms and culture medium are brought in physical contact when the fragible ampule is crushed. Chromatography grade filter paper is a preferred material for the carrier and has been employed in the manufacture of biological indicator process monitors for numerous years. The physical and chemical properties vary between various grades of filter papers. The selection of filter paper may influence the calibration of the biological monitor. Selection of a preferred material is made based on the historical experience with commercial sources such as Schleicher & Schuell or Whatman Ltd. Alternative materials for the carrier include any porous or capillary filled material that would passively transport the culture medium to the spores.

The culture medium is an aqueous solution/suspension of nutrient components to promote growth of viable microorganisms that may exist after the sterilization process that is being challenged by the device of the present invention. An example of a suitable culture medium is soybean casein digest broth that contains tryptone, soytone, dextrose, potassium phosphate dibasic, sodium chloride, and a pH indicator or other suitable growth detector. Formulations for culture media are widely known by those familiar with the state of the art. The detector or indicator provides a means to visually amplify the growth of microorganisms in the culture medium by changing the color of the medium. Numerous pH or oxidation-reduction dyes including Phenol red, have been cited in the literature as being commercially applicable detectors.

While the invention has been described in detail with respect to specific embodiments thereof, it will be understood by those skilled in the art that variations and modifications may be made without departing from the essential features thereof.

What is claimed is:

1. A sterility indicator which comprises:

(a) a means defining an elongated outer compartment having liquid impermeable and substantially non-gas absorptive walls, said compartment having a closed end and a first opening at a distal end thereof and at least one additional opening covered with a heat stable, gas transmissive and bacteria-impermeable material disposed at least partially around the perimeter of said outer compartment allowing sterilant vapor to pass through and into said outer compartment and located near said first opening, with a predetermined number of viable microorganisms suitable for monitoring steam sterilization being confined within said outer compartment adjacent said additional opening, and a predetermined number of viable microorganisms suitable for monitoring gas sterilization being confined within said outer compartment away from said additional opening and opposite said distal end:

(b) a closure member normally closing said first opening and movable to a second position to also close said additional opening; and (c) an inner compartment containing a nutrient medium disposed within said outer compartment with said nutrient medium being out of direct contact with said microorganisms, said inner compartment being adapted to open in response to external pressure thereby permitting said nutrient medium to contact said microorganisms.

2. The indicator of claim 1 in which the microorganisms are contained on an elongated carrier means.

3. The indicator of claim 1 in which the microorganisms are contained on opposite ends of an elongated absorbent wick.

4. The indicator of claim 1 in which the microorganisms positioned opposite the distal end are suitable for monitoring ethylene oxide.

5. A sterility indicator which comprises in combination;

(a) means defining a transparent deformable outer plastic shell having liquid impermeable and substantially non-gas absoptive walls, said shell having a first and second compartment which communicate through a channel, said first compartment having at least one opening therein and containing a predetermined number of viable microorganisms suitable for monitoring steam sterilization contained at one end of an absorbent wick, and a predetermined number of viable microorganisms suitable for monitoring gas sterilization contained at the opposite end of said wick and located in said second compartment, (b) said first compartment containing at least one gas transmissive, bacteria-impermeable opening in the form of a submicron screen with the end of said wick which contains said viable microorganisms suitable for monitoring steam sterilization being confined adjacent said screen, and the end of said wick which contains the gas sterilization monitoring microorganisms being positioned away from said screen in said second compartment, (c) a frangible glass ampule containing an aqueous nutrient medium disposed within said second compartment, said ampule being adapted to fracture upon deformation of said outer compartment thereby permitting said nutrient medium to contact said microorganisms through said wick, and (d) a flexible or semi-rigid cover member which seals around said two compartments and said channel forming a liquid containing member.

* * * * *